(12) United States Patent
Wustefeld (10) Patent No.: US 9,001,330 B2
(45) Date of Patent: Apr. 7, 2015

(54) ATTACHMENT FOR PLACEMENT ONTO AN OPTICAL SENSOR AND METHOD OF OPERATING AN OPTICAL SENSOR

(71) Applicant: Sick AG, Waldkirch/Breisgau (DE)

(72) Inventor: Martin Wustefeld, Sexau (DE)

(73) Assignee: Sick AG, Waldkirch/Breisgau (DE)

( * ) Notice: Subject to any disclaimer, the term of this patent is extended or adjusted under 35 U.S.C. 154(b) by 0 days.

(21) Appl. No.: 13/785,873

(22) Filed: Mar. 5, 2013

(65) Prior Publication Data

US 2013/0235379 A1    Sep. 12, 2013

(30) Foreign Application Priority Data

Mar. 7, 2012  (EP) .................................... 12001541

(51) Int. Cl.
 *G01N 21/00* (2006.01)
 *G01N 21/59* (2006.01)
 *G01S 7/497* (2006.01)
 *G01N 21/47* (2006.01)

(52) U.S. Cl.
 CPC ................ *G01N 21/59* (2013.01); *G01S 7/497* (2013.01); *G01N 21/47* (2013.01)

(58) Field of Classification Search
 CPC ... G01N 21/47; G01N 21/59; G01N 21/8483; G01N 35/00029; F16K 37/0083
 USPC ................ 356/435, 607–608, 614, 622, 629, 356/639–640, 445, 3.11, 4.01, 141.1; 235/462.17, 462.24, 454, 470, 467, 235/472, 462.31–462.32, 462.36, 462.38; 250/559.23, 559.19
 See application file for complete search history.

(56) References Cited

U.S. PATENT DOCUMENTS

| | | |
|---|---|---|
| 5,455,669 A | 10/1995 | Wetteborn |
| 6,812,450 B2 | 11/2004 | Hipp |
| 7,428,995 B1 | 9/2008 | Stern et al. |
| 7,570,361 B2 | 8/2009 | Schneider et al. |
| 2002/0018198 A1 | 2/2002 | Pierenkemper |
| 2007/0131842 A1 | 6/2007 | Ernst |

(Continued)

FOREIGN PATENT DOCUMENTS

| | | |
|---|---|---|
| DE | 39 08 273 C1 | 5/1990 |
| DE | 4345448 C2 | 7/1998 |

(Continued)

OTHER PUBLICATIONS

Translation of European Search Report, Application No. EP 12 00 1541, dated Jun. 21, 2012, five (5) pages.

(Continued)

*Primary Examiner* — Tri T Ton
(74) *Attorney, Agent, or Firm* — Nath, Goldberg & Meyer; Jerald L. Meyer; Sanjana Mangalagiri (57) ABSTRACT

The invention relates to an attachment for placement onto an optical sensor having a housing with an inlet opening for the entry of detection light into the attachment, a test light receiver for receiving light incident at the test light receiver and for a power measurement of the light incident at the test light receiver as test light and having a signal outputting device for outputting an output signal correlated to the test light power. The invention moreover relates to a combination of an optical sensor and such an attachment and to a method for operating an optical sensor which method can be carried out with such an attachment.

12 Claims, 5 Drawing Sheets

(56) References Cited

U.S. PATENT DOCUMENTS

| 2009/0108070 A1 | 4/2009 | Zhang et al. |
| 2009/0140047 A1 | 6/2009 | Yu et al. |
| 2012/0218564 A1 | 8/2012 | Wüstefeld et al. |

FOREIGN PATENT DOCUMENTS

| DE | 198 00 968 A1 | 7/1999 |
| DE | 103 13 194 A1 | 10/2004 |
| EP | 0 122 609 A1 | 10/1984 |
| EP | 1 239 301 A1 | 9/2002 |
| EP | 1 939 650 A2 | 7/2008 |
| EP | 1 980 871 A1 | 10/2008 |
| EP | 2 003 471 A1 | 12/2008 |
| EP | 2 053 538 A1 | 4/2009 |
| EP | 2 182 378 A1 | 5/2010 |
| EP | 2 394 882 A1 | 12/2011 |

OTHER PUBLICATIONS

Primes Katalog Laserdiagose, Produkte und Dienstleistungen, (2011), pp. 1-59.

8230 Optical Power Meter, (2009), ADCMT, pp. 1-6, http://www.adcmt-e.com.

ATTACHMENT FOR PLACEMENT ONTO AN OPTICAL SENSOR AND METHOD OF OPERATING AN OPTICAL SENSOR

FIELD OF INVENTION

The invention relates to an attachment for placement onto an optical sensor, to a combination of an optical sensor and such an attachment and to a method of operating an optical sensor on use of such an attachment.

BACKGROUND INFORMATION

Known optical sensors comprise e.g. a transmission unit for the transmission of detection light into a detection region, a receiver for receiving light reflected or remitted from the detection region and an evaluation unit for evaluating the reflected or remitted light. In this respect it can be e.g. a scanner system such as are described in DE 198 00 968 C2, EP 1 980 871 B1 or DE 39 08 273 C1 or distance measuring sensors which can, e.g. determine the distance from the light duration which a light signal transmitted into a monitoring zone takes after reflection from an object in the monitoring zone back to the sensor.

Other optical sensors are designed as light barriers or light grids which detect the presence of an object in a monitoring zone by interruption of a light beam or reflection of the light beam from the monitoring zone.

For monitoring the functionality, in particular for the reliable object detection and object localization in a safety system a control of the most important power functions is required. In known solutions test objects are provided in the monitoring zone of the sensor for this purpose and it is checked before or during the measurement whether these test objects are correctly observed.

The presence of such test objects in the monitoring zone can, however, even be detrimental to the monitoring itself.

SUMMARY OF THE INVENTION

It is the object of the present invention of providing a possibility of reliably checking the functionality of an optical sensor or parts thereof.

This object is satisfied by an attachment having the features of claim 1 and/or a method of operating an optical sensor. Claim 14 is directed at a combination of an optical sensor having an attachment in accordance with the invention. Preferred embodiments and designs are the subject of dependent claims.

An attachment in accordance with the invention serves for the placement onto an optical sensor which has a transmission unit for the transmission of the detection light into a detection region, a receiver for receiving light reflected or remitted from the detection region or light transmitted through the detection region and an evaluation unit for evaluating the received light.

If the transmission unit and the receiver are not integrated into a unit—this means that then, for example, a monitoring zone is monitored in transmission geometry—then the placement of the attachment onto the optical sensor means the placement onto that part which comprises the transmission unit.

An attachment in accordance with the invention can correspondingly also be brought into the optical path of the detection light in already existing optical sensors and can thereby ensure its functional safety.

The attachment in accordance with the invention has a housing with an inlet opening for the inlet of detection light into the attachment. Through this inlet opening the detection light of the optical sensor can enter into the attachment.

A test light receiver for receiving light incident as test light and for the power measurement of light incident as test light onto the test light receiver, which test light comprises at least a part of the detection light of the optical sensor, is arranged within the housing of the attachment in accordance with the invention. A signal outputting device serves for the output of an output signal correlated to the test light power. Within the attachment thus at least a part of the detection light is deflected to a test light receiver and is measured and evaluated there as test light. Since the signal outputting device of the attachment generates its own signal dependent on the test light power the safety is significantly increased.

The attachment in accordance with the invention thus makes a possibility available of continuously checking the functionality of an optical sensor through an external unit. If the measured power signal of the test light receiver does not coincide with an expected signal, e.g. stored in a memory, one has to assume a functional failure of the sensor, this means e.g. an erroneous function of the transmission unit of the optical sensor.

For this purpose the signal outputting device of a first embodiment of the attachment can be configured for the generation and output of a power signal dependent on the measured power of the test light. This power signal can e.g. be evaluated by the evaluation unit of the optical sensor. If one can determine that an erroneous function of the sensor is present from the power signal, this means that e.g. the power zero is measured, the evaluation unit of the optical sensor can e.g. output a warning signal to a user or a stop signal to a dangerous machine. For this purpose, the attachment can be connected to the evaluation unit of the optical sensor via a corresponding signal line. In this manner the anyway present evaluation unit of the optical sensor can be used in a simple and cost-effect manner also for the functional monitoring by the attachment. The evaluation unit of the optical sensor which serves the purpose of evaluating signal of the optical sensor, for example of a safety sensor, anyway has a function for the outputting of a warning signal and/or stop signal, when the optical sensor e.g. determines an unallowed object in its monitoring zone.

For an alternative embodiment the attachment itself has a test light evaluation unit for evaluating the test light power measured with the test light receiver. The signal outputting device can be configured in order to output, for example, a warning signal directly to a user and/or to output a stop signal directly to a dangerous machine in dependence on the evaluation result of the test light evaluation unit. In this example the test light evaluation unit of the attachment thus itself evaluates the power signal of the test light receiver and the attachment itself generates the possibly required output signal, so that in this example an evaluation unit of the optical sensor is not required for the function of the attachment.

If an own warning signal and/or stop signal is generated by the signal outputting device of the attachment, the attachment works inherently safe and is not dependent on the functionality of the evaluation unit of the optical sensor.

The attachment in accordance with the invention must be arranged such that it is present in the optical path of the detection light at least at a predetermined point in time. Advantageously a fastening device is provided for this purposes which enables the fastening of the attachment at the optical sensor and/or at its part comprising a transmission unit. In this respect it can, for example, be a mechanical connection possibility, for example, a screwed connection, a clamping connection or a latch-on connection. Also magnetic connections are, for example, possible. For this purpose, a design of the attachment has a magnet which can interact with a metallic part of the optical sensor (or vice versa).

A preferred embodiment of the attachment in accordance with the invention has an exit opening for the exit of detection light from the attachment into the detection region. In this respect a dividing mirror is provided in the optical path between the inlet opening and the exit opening in this preferred embodiment with the aid of which a part beam of the detection light can be decoupled as test light such that it is deflected to the test light receiver at least at a point in time. For such an embodiment it is ensured that only a part of the detection light is deflected to the test light receiver. The other part is available for the detection function of the optical sensor after exit from the attachment.

Such an embodiment can, for example, be advantageous for an optical sensor having a fixed optical path, such as, for example, a light barrier or a distance measuring sensor which works on the principle of time of flight of light. It can, however, also be advantageously used in scanner systems as will be explained in the following.

Generally the dividing mirror can be arranged in the attachment of this embodiment so that it deflects the decoupled part light permanently in the direction of the test light receiver. Such a design has the advantage that no additional mechanically movable elements have to be present in the attachment. However, it can also be advantageous when the dividing mirror is movable, in particular rotatable about an axis which corresponds to the optical path of the detection light in the attachment. The decoupled test light is then incident at the test light receiver at periodic spacings in dependence on the rotary speed of the dividing mirror. Thereby, also the timely extent of the incident light beam at the test light receiver is available as evidence of the functionality of the optical sensor, so that the safety can be further increased. Through the rotation of the dividing mirror in particular a frequency is provided which enables a very good discrimination of the test light in this optical sensor. The expected extent can be checked well from the speed of the rotatable dividing mirror and can, e.g. be differentiated well from interfering light with reference to the frequency of the rotation of the dividing mirror.

The term housing should not necessarily be understood as a closed housing in the following text. When e.g. the optical sensor and the attachment are used in an atmosphere clean per se, a sealed closure of the housing is not required but it is sufficient, for example, to have a housing in the form of corresponding support elements which support the functionally relevant components of the attachment, i.e. in particular the test light receiver and—for a corresponding design—the dividing mirror.

However, a preferred design provides that the attachment has a closed housing which is sealed off to the outside at least after the connection to the optical sensor. This ensures a high functional safety, since no contamination can arise within the attachment.

A preferred design of an embodiment having a dividing mirror provides that the outlet opening has a closed transparent outlet window from which the part of the detection light which is not decoupled by the dividing mirror in the direction of the test light receiver exits the attachment.

Preferably this transparent outlet window is not arranged perpendicular to the optical path of the detection light and is thus illuminated obliquely by the detection light. In this manner it is ensured that the outlet window does not lead to an undesired reflection back to the optical sensor.

Advantageously, it can moreover be provided that the outlet window has a device for monitoring the window contamination which can e.g. provide a signal to the evaluation unit of the optical sensor when a window contamination of the outlet window has been determined. Once the functionality of the optical sensor having the pre-switched attachment is no longer ensured a warning signal and/or stop signal can then in turn be output to a user and/or to a machine by the evaluation unit of the optical sensor.

Such an attachment having an outlet window monitored for contamination can advantageously also be used for an optical sensor which indeed has a sensor exit window, but not a sensor exit window monitored for contamination. Such an attachment having a window monitoring can thus significantly increase the safety of an optical sensor of inherently simple design without window monitoring.

For an embodiment of the attachment in accordance with the invention which is in particular suitable for an optical sensor designed as a scanner with a scan region, the attachment is designed such that it can be arranged in the scan region of the scanner so that at least a part of the detection light can arrive through the inlet opening of the attachment at the test light receiver at a point of time during the scan process.

In an optical scanner detection light, for example, is sent into the scan region, for example, with the aid of a pivotable deflection unit in a manner known per se, such that the light beam covers this periodically. From the light that is reflected or remitted from the scan region back in the direction of the scanner one can then determine the presence of an object in the scan region. Depending on whether an object is allowed to be present at that position or not a corresponding signal can be generated and output. The scan region of the scanner is in this connection defined by the spatial region which is covered by the detection light during a scan process. From the likewise measured light propagation time between scanner, object and back to the scanner one can moreover determine the distance to the object.

The scan region does not necessarily have to coincide with the spatial region which is to be monitored in this manner. An attachment in accordance with the invention which is, in particular used for the monitoring of the functionality of such a scanner can, for example, be arranged in a part of the scan region which does not have to be monitored for the presence of objects. During a complete scan process the detection light can then enter into the attachment at a certain point in time and can be guided to the test light receiver there and be used in the described manner for the monitoring of the functionality.

When the attachment is present in an angular region of the scanner which does not belong to the monitored zone the complete detection light can be used in this angular region in the attachment as test light.

Alternatively it is also possible that an attachment is used with a scanner in which, for example, a part of the detection light is decoupled with the aid of a dividing mirror and is guided to a test light receiver as is described above. Such an embodiment having a dividing mirror has an outlet window through which the part of the detection light not deflected towards the test light receiver can exit again and is then available for the object detection in the monitoring zone of the scanner. Such an attachment can, however, also be used when it is present in an angular region of the scanner which belongs to the monitoring zone. Depending on the requirement it must then be considered on the evaluation of the signals of the optical sensors that only a weaker light power enters into the monitoring region in the angular region in which the attachment is present.

For a method in accordance with the invention for operating an optical sensor, detection light is transmitted into a detection region and light remitted or reflected from the detection region or light transmitted through the deflection region is evaluated for the formation of a detection signal. An attachment is arranged in the optical path of the detection light in which attachment at least a part of the detection light of the optical sensor is guided to a test light receiver as test light, with the test light receiver being configured for the reception and for the power measurement of the test light. An output signal correlated to the test light power is then output by the attachment.

In the method in accordance with the invention it is thus possible to check the functionality of the optical sensor during the detection process of the optical sensor with an additional attachment. The advantages of a method in accordance with the invention result from the same advantages described above in connection with the attachment in accordance with the invention.

Preferred designs of the method in accordance with the invention result in an analog manner from the preferred embodiments of the attachment in accordance with the invention.

It can in particular be provided that the output signal correlated with the test light power is directly introduced into the evaluation unit of the optical sensor used, such that this can read from the output signal correlated with the power of the test light, whether an erroneous function of the sensor is present, thus, whether, for example, the power zero is measured. The evaluation unit of the optical sensor can then, for example output a warning signal to a user or a stop signal to a dangerous machine.

A different design of the method in accordance with the invention provides that the attachment itself evaluates the signal of the test light receiver in order to detect whether the test light power corresponds to the expected value. If this is not the case a corresponding warning signal or stop signal can be output directly from the attachment for this design of the method. This design thus enables an inherently safe operation of the attachment which is independent of the functionality of the optical sensor and in particular of its evaluation unit.

The method in accordance with the invention can, for example, be used with an optical sensor which is designed as a scanner. For this purpose, the attachment is attached in a region of the scan region in the optical path of the detection light which advantageously, for example, does not have to be monitored for the presence or absence of an object. In this manner, the detection light will enter through the inlet window into the attachment at a predetermined point in time during a scan process and will be incident on the test light receiver in order to be evaluated there with regard to its power in the described manner.

On the other hand, it is also possible to use the method in accordance with the invention in an attachment in which a dividing mirror is provided by means of which only a part of the detection light is decoupled in the attachment and is guided to a test light receiver in order to be evaluated there in the described manner. Such a method can, for example, be used, when the optical sensor is a scanner and the attachment is arranged in a region of the scanning angle which does not have to be monitored for the presence or absence of objects. Through the use of the dividing mirror it is ensured that also for decoupling of a part of the detection light that a portion of the detection light can still pass through the attachment into the detection region of the optical detector.

The invention will be described in detail by means of the attached drawings which show schematic illustrations of the embodiments in accordance with the invention. Components corresponding respectively to one another are referred to using the same reference numerals. There is shown.

BRIEF DESCRIPTION OF THE DRAWINGS

DETAILED DESCRIPTION

Figure 1:
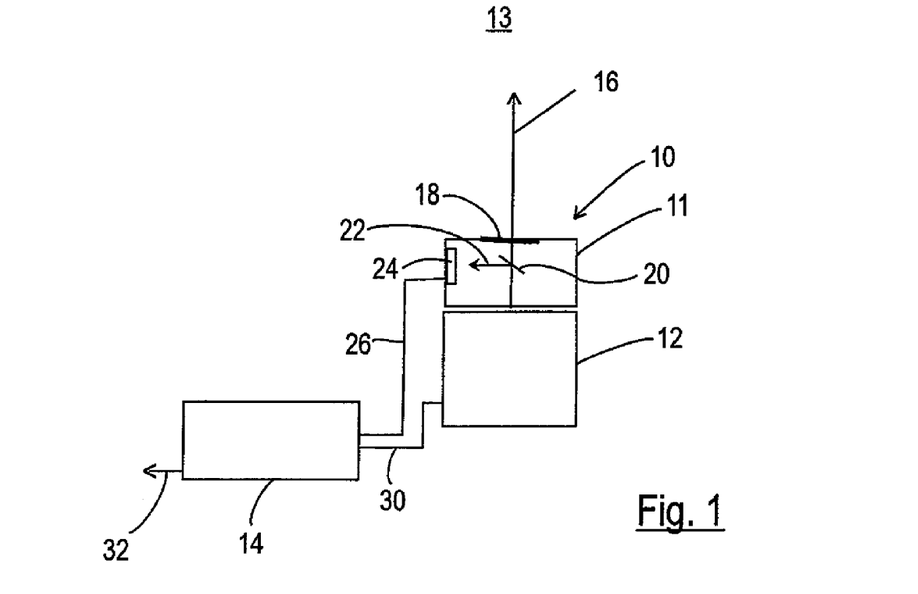
FIG. 1 a first embodiment of an attachment in accordance with the invention.

An optical sensor 12 known per se is shown in FIG. 1 which has a transmission light source, e.g. a laser diode, which transmits detection light 16 in a direction of a detection region 13. A signal of this optical sensor 12 is provided to an evaluation unit 14 via a signal line 30. Alternatively the evaluation unit can also be provided in an integrated manner in the optical sensor 12.

The optical sensor 12 can, e.g. be a distance measurer which determines the distance to a reflected object in the detection region from the propagation time of light retransmitted from the detection region 13. For this purpose the optical sensor 12 has a receiver in a manner known per se whose signal is correspondingly evaluated by the evaluation unit 14.

However, the optical sensor can e.g. also be a light barrier. In such a case e.g. the detection light 16 is incident on a reflector at a known position in the detection region 13 and the reflected light is evaluated. If e.g. no reflected light is determined then one must assume that the path between the sensor 12 and the reflector is no longer free. A design is not shown in which the detection light 16 is incident on a remote receiver and—when the light can no longer be detected at the receiver—one has to assume that a blocking of the light path between the sensor and the remote receiver is present.

Finally, the optical sensor 12 can also be a scanner which is moved such that it covers a spatial region in a manner known per se with a light beam and which evaluates light reflected from the spatial region for object detection. Corresponding embodiments are described in the following with reference to FIGS. 6 to 9.

Depending on the application and requirement the evaluation unit 14, for example, outputs a warning signal or a stop signal 32 to a machine e.g. when an unallowed object is present in the detection region.

The attachment 10 is present in the optical path of the detection light, with the attachment 10 having a closed housing 11 in the present example. The attachment can, e.g. be directly attached at the optical sensor 12 with the aid of a corresponding fastening device.

For reasons of clarity, the outlet window of the optical sensor 12 for the detection light 16 and the inlet window to the attachment 20 are not explicitly illustrated.

The detection light 16 is incident through the transparent outlet window 18 of the attachment 10 into the adjoining detection region 13 which should be monitored. A part 22 of the detection light 16 is decoupled from the optical path and is guided to a light receiver 24, for example, a photodiode or an array of photodiodes with the aid of a semi-permeable mirror 20 arranged obliquely in the optical path. The signal of the light receiver 24 is sent to the evaluation unit 14 via a signal line 26.

This can then evaluate the measured power of the decoupled part light 22 at the light receiver 24. If the power does not correspond to the expected power the evaluation unit 14 of the optical sensor 12 can likewise output a warning signal and/or stop signal via the signal output 32. This is e.g. the case when the light source of the optical sensor is defect or no longer provides the desired power. A correct function of the optical sensor 12 is then no longer ensured so that an erroneous function is determined in this manner and can then be processed for the generation of a corresponding signal at the signal output 32.

Both the outlet window 18 of the attachment and also the outlet window of the optical sensor 12 and the inlet window of the attachment 10 can respectively be obliquely arranged in order to avoid reflections back into the receiver of the optical sensor 12.

Figure 2:
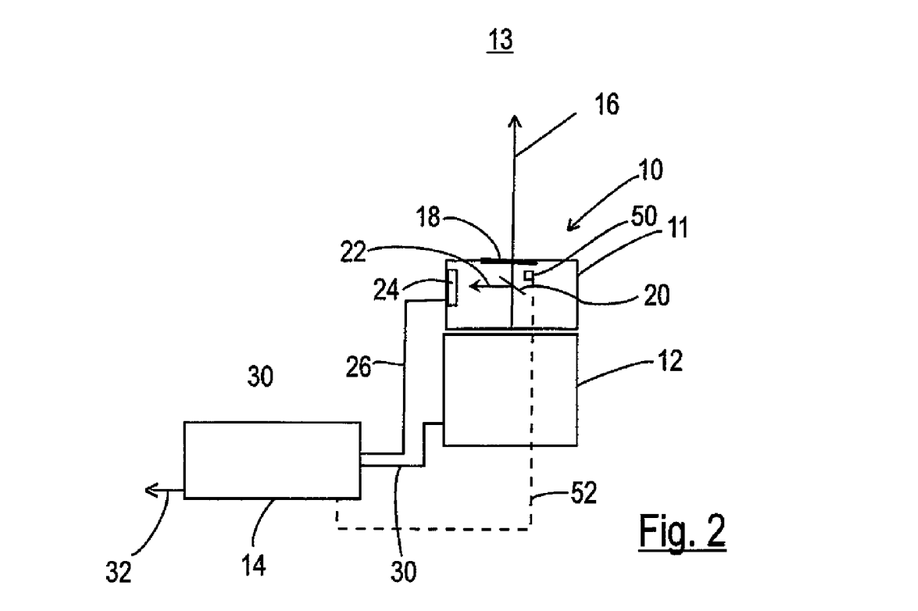
FIG. 2 a second embodiment of an attachment in accordance with the invention.

FIG. 2 shows a variation of the first embodiment of FIG. 1 having an additional unit 50 for monitoring the contamination of the outlet window 18 of the attachment 10. The unit 50 for monitoring the contamination of the window can e.g. evaluate the reflections of a light signal at the outlet window 18 in order to determine its degree of contamination.

A different variant, which is not illustrated, in which the unit comprises a signal transmitter on the one side of the outlet window and a signal receiver at the other side of the outlet window, so that the transmission of the outlet window can be measured.

A signal line 52 serves for the transfer of the signal of the unit 50 for monitoring the degree of contamination at the outlet window 18 at the evaluation unit 14 of the optical sensor 12. When e.g. the outlet window 18 has too strong a contamination the evaluation unit of the optical sensor 14 can likewise generate a warning signal and/or stop signal in this manner, since the functionality can no longer be ensured.

The inlet window of the attachment can naturally likewise be monitored for contamination with the aid of a corresponding unit, wherein the danger of the contamination is smaller in this example, since the attachment directly adjoins at the optical sensor 12 having its inlet window for the shown embodiment.

Figure 3:
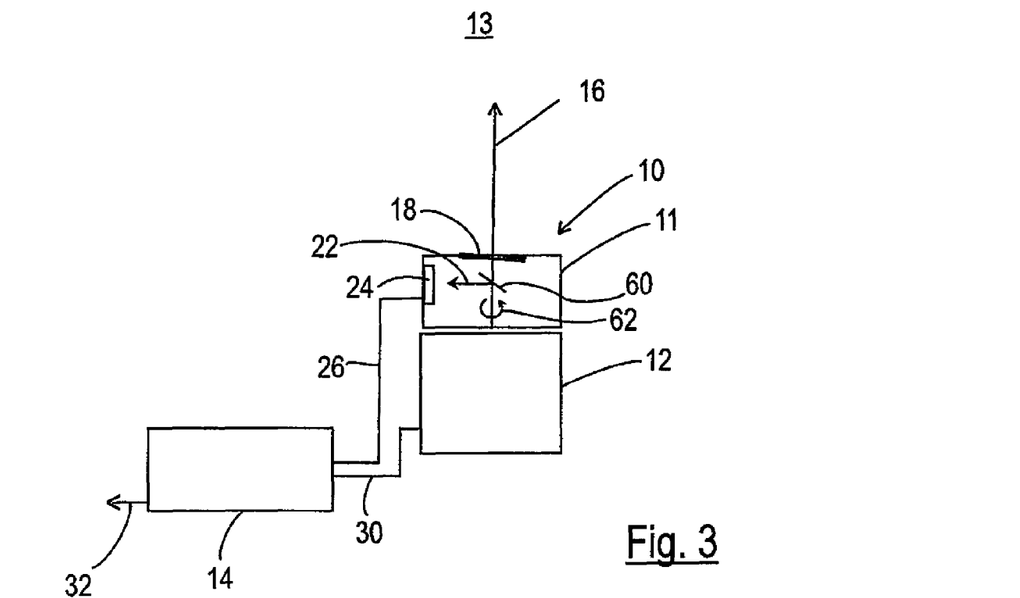
FIG. 3 a third embodiment of an attachment in accordance with the invention.

In a variant of the design of FIG. 1, FIG. 3 shows a movable dividing mirror 60 arranged obliquely in the optical path which rotates in the direction of rotation 62 about the beam direction of the detection light 16. The part light 22 decoupled is incident at periodic spacings on the test light receiver 24 on a continuous rotation of the dividing mirror 60 and it is correspondingly detected and evaluated at corresponding periodic distant spaces. The test signal can be discriminated and evaluated very well from the timely extent of the signal at the test light receiver 24, with the aid of the evaluation unit 14. If the test light signal is not as expected, a warning signal and/or stop signal can in turn be generated at the output 32.

Figure 4:
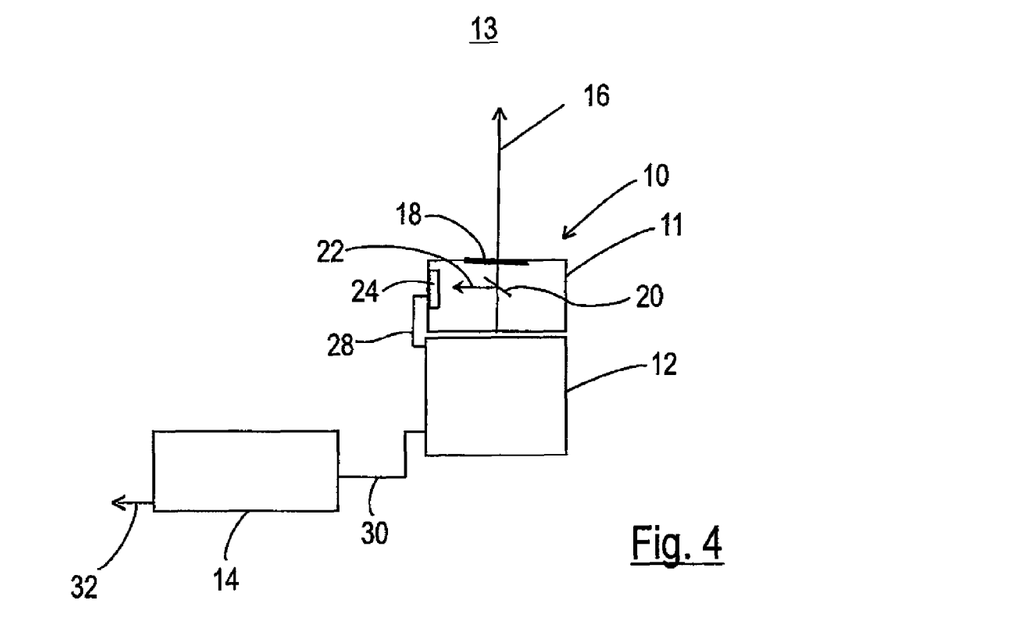
FIG. 4 a fourth embodiment of an attachment in accordance with the invention.

FIG. 4 shows a design in which the signal of the test light receiver 24 is introduced in the optical sensor 12 with the aid of a signal line 28 in order to be guided to the evaluation unit 14 of the optical sensor via the signal line 30. Such a design can, for example, provide that on the attachment of the attachment 10 at the optical sensor 12 a plug connection is closed which then represents the signal line 28.

Figure 5:
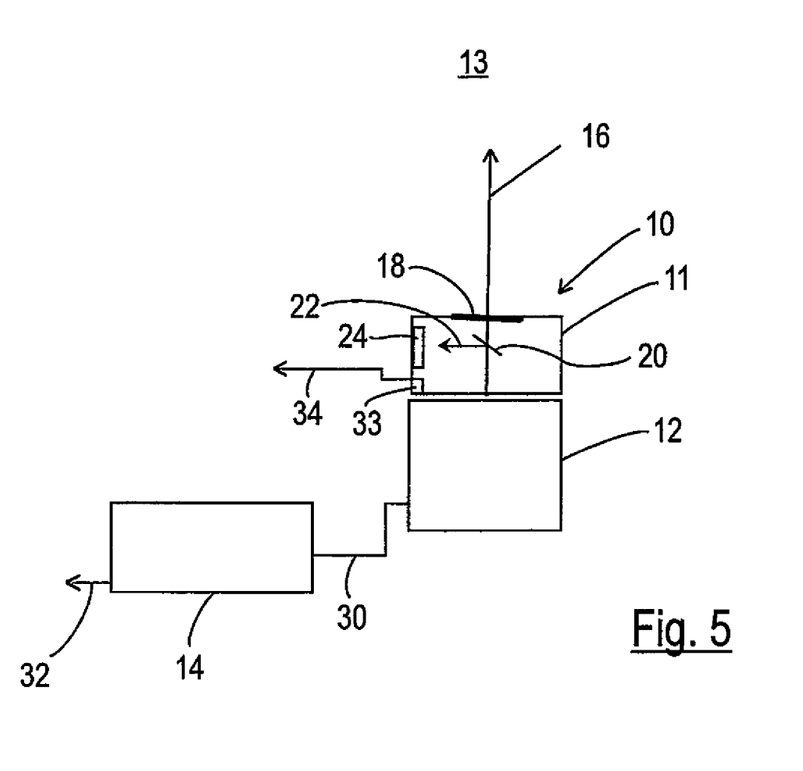
FIG. 5 a fifth embodiment of an attachment in accordance with the invention.

FIG. 5 finally shows an embodiment as a variant of the embodiment of FIG. 1 in which the attachment 10 itself possesses an evaluation unit 33 into which the signal of the test light receiver 24 is introduced and with whose aid a warning signal and/or stop signal can be generated. Such a design of the attachment 10 requires no connection to the evaluation unit 14 of the optical sensor 12 and therefore ensures a secure monitoring of the optical sensor 12 independent of the function and functionality of the evaluation unit 14.

The test light evaluation 33 can, for example, be a correspondingly programmed microprocessor. Alternatively, also a threshold value detection for checking the light power received by the test light receiver 24 can be implemented.

For reasons of clarity the signal connection between the test light receiver 24 and the test light evaluation unit 33 is not shown in FIG. 5 which signal connection is provided within the attachment for this embodiment.

The features of the individual embodiments in particular described in the FIGS. 1 to 5 can also be combined in a different composition. Thus, for example, also the designs of FIGS. 3 to 5 can have a unit for monitoring the outlet window as is described with reference to FIG. 2. Also a movable dividing mirror as is described with reference to FIG. 3 can be provided in the different designs, for example of FIGS. 1, 2, 4 and 5.

The FIGS. 6 to 9 are directed at embodiments in which the attachment in accordance with the invention is used for an optical scanner 120.

Optical scanners as are shown, for example in FIGS. 6 to 9, are generally known. The scanner 120 comprises a beam generation and deflection unit 122 within which a light beam 160 is generated in a manner known per se which will be referred to in the following as detection light. The beam generation and deflection unit 122 is designed such that the detection light beam 160, which can, for example, comprise laser light, covers a detection region which is formed in the present example by the scan region 130. If, e.g. an object is present in this scan region 130 then the light which is transmitted into the scan region at a corresponding scan angle is reflected and can be detected in a manner known per se by a detector within the scanner 120. In this manner, the angular position of an object in the scan region 130 can be determined. If moreover, the light propagation time of a light pulse from the scanner 120 to the reflecting object and back is measured, one can so determine the distance to the object with the aid of the speed of light.

In this connection, the scanner 120 is designed such that the detection light beam 160 which periodically covers the scan region 130 exits through a front disc 126 into the scan region. The front disc can, for example, be a semi-circularly shaped glass disc. The scanner 120 transmits the measured signals on the presence or absence or on the position of the object in the scan region via the signal line 30 to an evaluation unit 14 which likewise in a manner known per se processes the corresponding information in order to generate, for example, a warning signal and/or stop signal, possibly also via the signal output 32, when an unallowed object is present in the scan region.

Figure 6:
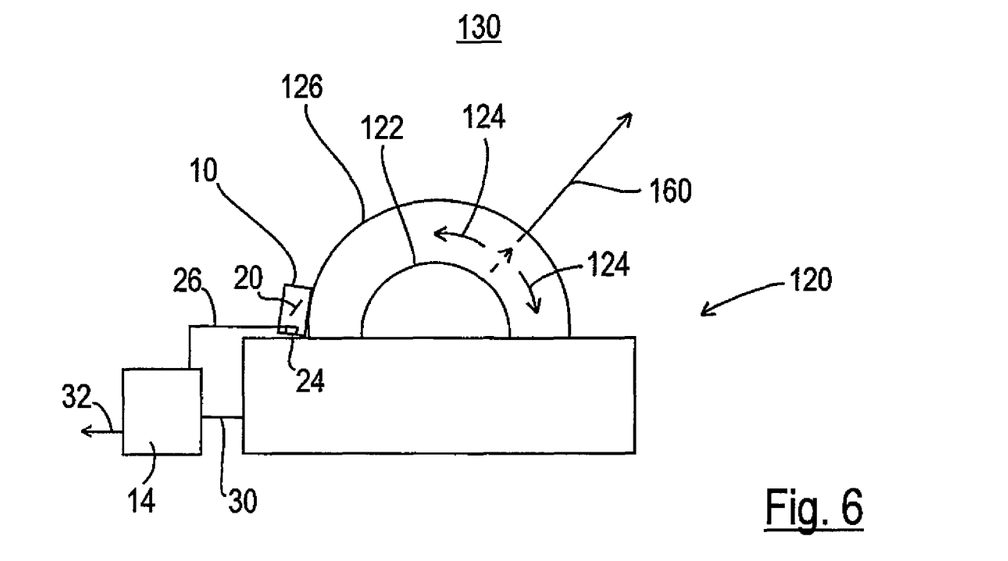
FIG. 6 an attachment in accordance with the invention on use with a scanner in a first state.

In a boundary region of the scan region an attachment 10 is provided in the embodiment in accordance with the invention described with respect to FIG. 6 which is built up similar to the attachment 10, for example, of FIG. 1, 2, 3, 4 or 5. For the embodiment in accordance with FIG. 6 it likewise has (for reasons of clarity not referred to with reference numerals in this example) a housing 11, a dividing mirror 20 and a light receiver 24. Moreover, the attachment 10, like the attachment 10 of FIGS. 1 to 5, also has an inlet window and an outlet window 18 which are not illustrated for reasons of clarity in FIG. 6.

Figure 7:
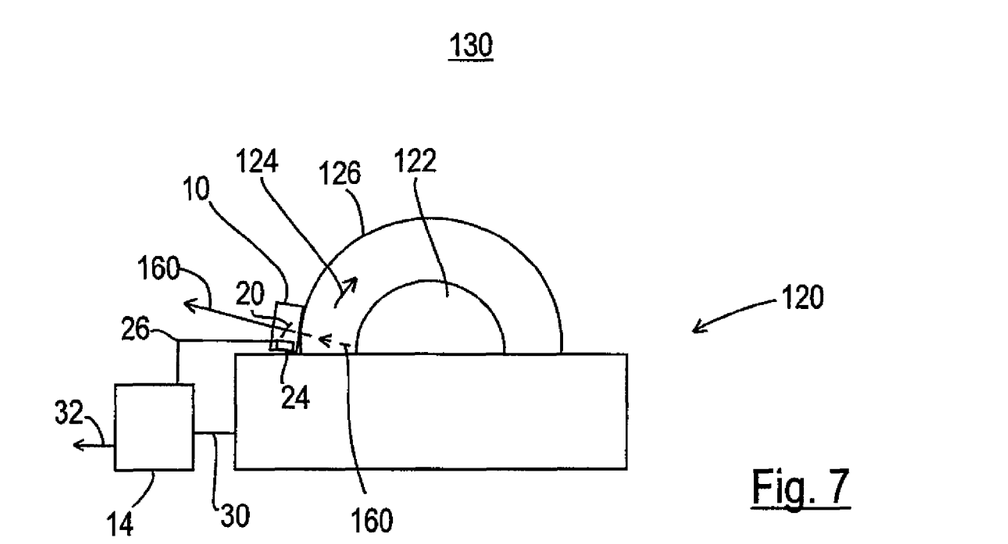
FIG. 7 the embodiment of FIG. 6 in a different state.

FIG. 7 shows the same embodiment in a different operating state. The detection light beam 160 of the scanner 120 is present here in a different position in which it enters into the attachment 10 through the front disc 126 of the scanner 120 and the inlet window of the attachment 10. A part of the light is deflected onto the light receiver 24 with the aid of the dividing mirror 20 and can be further processed there in a manner as is described with regard to the embodiments of FIGS. 1 to 5. If an attachment which has a test light evaluation unit 33 is used with a scanner 120 a warning signal or a stop signal is directly output via a signal output line 34 as is described above with reference to FIG. 5. If it is found that the light power measured at the light receiver 24 at this point in time during the scanning process does not correspond to an expectation, a determination is made that an error is present in the system, for example, a malfunction of the beam generation unit of the scanner 120. The evaluation unit 14 of the optical sensor is possibly informed of this via the signal line 26 and can, for example, output a corresponding warning signal and/or stop signal via the signal output 32.

Those parts of the detection light 160 which are not deflected to the light receiver 24 exit from the attachment 10 again, as is described with reference to the FIGS. 1 to 5, and are available for object detection by the scanner 120.

The attachment 10 is attached in this example, for example, at the front disc 126 or by means of a corresponding attachment device at the scanner 120, for example in a clamped manner, in an engaged manner or the like.

Figure 8:
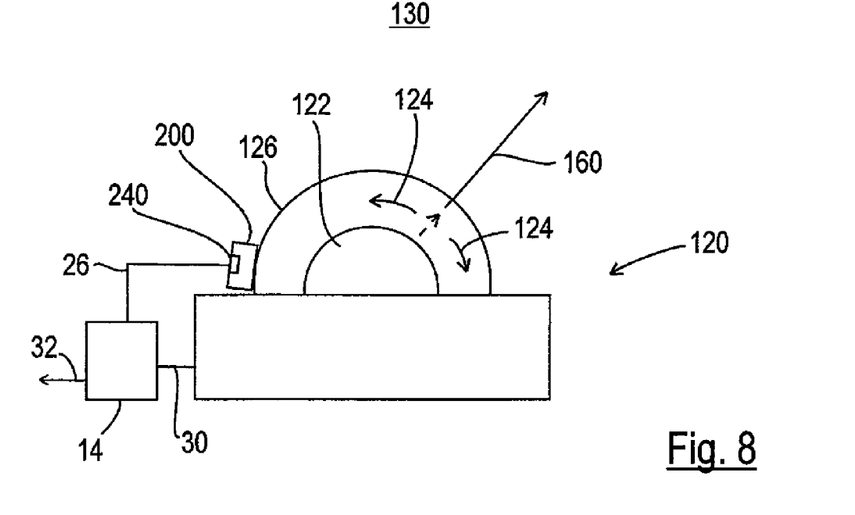
FIG. 8 a different embodiment of an attachment in accordance with the invention on use with an optical scanner in a first state.

FIG. 8 shows an embodiment in which the attachment 200 is arranged at a position of the scan region covered by the detection light beam 160 which does not have to be monitored. In this regard it is not damaging for such an application when the detection light 160 can no longer exit from the attachment 200 in order to be available for an object detection with the aid of the scanner 120. Such a region can, for example, lie in a small angular region of the boundary of the scan region amounting to 180° in the present example.

Figure 9:
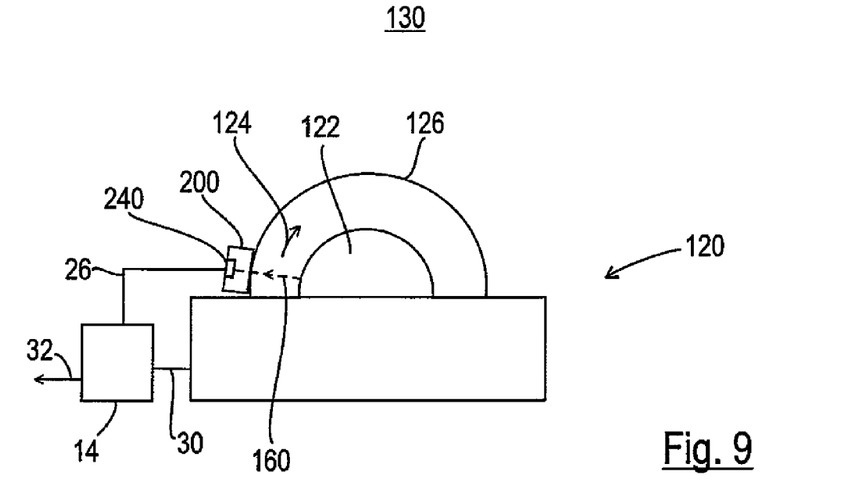
FIG. 9 the design of FIG. 8 in a different state.

FIG. 9 shows a state in which the detection light 116 enters into a correspondingly designed attachment 200 through the inlet window not illustrated in this example. It is incident there directly on the light receiver 240, which is similar to the light receiver 24 described with respect to the FIGS. 1 to 7, can generate a power signal and can be guided to the evaluation unit 14 of the optical scanner 120 via the signal line 26 (or via a plug connection similar to the plug connection 28 described above with reference to FIG. 4).

In a non-illustrated variant of this embodiment the attachment 200 has a test light evaluation unit 33 as is described with reference to FIG. 5 which can directly generate a warning signal or stop signal.

The embodiments described with reference to FIGS. 1 to 5 can be used with such sensors in which, for example, the detection light beam remains spatially unchanged, as is, for example, the case for a light barrier or light grid. The variants of FIGS. 6 to 9 relate to examples of a two-dimensional scanner, wherein the attachment can, for example, be used for checking the functionality of the beam generation unit. An attachment in accordance with the invention can also be used with the different sensors (for example, for distance-measuring sensors on the basis of the principle of time-of flight of light, for triangulation measurement arrangements for distance measuring etc.).

The attachment in accordance with the invention enables a continuous monitoring of the functionality of the optical sensor without this having to be specifically redesigned. The attachment can also be used with already present sensors, in order to, for example, make an optical sensor of simple design significantly more secure.

REFERENCE NUMERAL LIST 10 attachment
11 housing
12 optical sensor
13 detection region
14 evaluation unit
16 detection light
18 outlet window of the attachment
20 dividing mirror
22 decoupled test light
24 light receiver
26, 28, 30 signal line
32 signal output
33 test light evaluation unit
34 signal output
50 device for measurement of contamination
52 signal line
60 rotatable dividing mirror
62 direction of rotation
120 scanner
122 beam generation and deflection unit
124 pivot direction
126 front disc
130 detection region
160 detection light
200 attachment
240 light receiver

The invention claimed is:

1. An attachment for placement onto an optical sensor or onto a part thereof, wherein the optical sensor having a transmission unit for the transmission of detection light into a detection region; a receiver for receiving light reflected or remitted from the detection region or for receiving light transmitted through the detection region; and an evaluation unit for evaluating the received light, wherein the attachment comprises the following:

a housing having an inlet opening for the entry of at least a part of the detection light into the attachment;

a test light receiver for receiving detection light incident as test light and for the power measurement of the detection light incident as test light at the test light receiver;

a signal outputting device for outputting an output signal correlated with the test light power;

an outlet opening for the exit of detection light from the attachment into the detection region, wherein at least the outlet opening has a transparent outlet window;

a device for monitoring the window contamination of the outlet window; and a dividing mirror arranged in the optical path between the inlet opening and the outlet opening for decoupling a part beam from the detection light as test light such that the test light is deflected to the test light receiver at least at a point in time.

2. An attachment in accordance with claim 1, wherein the signal outputting device is configured for the generation and output of a power signal in dependence on the measured power of the test light to an evaluation unit of the optical sensor.

3. An attachment in accordance with claim 1, having a test light evaluation unit for evaluating the test light power measured with the test light receiver, wherein the signal outputting device is configured for the output of a warning signal or a stop signal in dependence on the evaluation of the test light evaluation unit.

4. An attachment in accordance with claim 1, having a fastening device for fastening the attachment at the optical sensor or at its part comprising a transmission unit in such a manner that it is at least present in the optical path of the detection light at a predefinable point in time.

5. An attachment in accordance with claim 1, wherein the dividing mirror is movable.

6. An attachment in accordance with claim 5, wherein the dividing mirror is rotatable.

7. An attachment in accordance with claim 1, wherein the outlet window is not arranged perpendicular to the optical path of the detection light in the attachment.

8. An attachment in accordance with claim 1, wherein the housing is designed such that it is substantially closed at least after placement onto the optical sensor.

9. An attachment in accordance with claim 1, wherein the attachment is designed to be arranged in a scan region of a scanner such that at least a part of the detection light arrives through the inlet opening of the attachment at the test light receiver at a point in time during a scanning procedure, wherein the scanning region of the scanner is defined by the spatial region which is covered by the detection light during a scanning process.

10. An attachment in accordance with claim 9, wherein it is an attachment for an optical sensor designed as a scanner having a scan region.

11. A combination of an optical sensor and an attachment for placement onto the optical sensor or onto a part thereof comprising a transmission unit, wherein the attachment comprises the following:
- a housing having an inlet opening for the entry of at least a part of a detection light into the attachment;
- a test light receiver for receiving detection light incident as test light and for the power measurement of the detection light incident as test light at the test light receiver;
- a signal outputting device for outputting an output signal correlated with the test light power;
- an outlet opening for the exit of detection light from the attachment into the detection region, wherein at least the outlet opening has a transparent outlet window;
- a device for monitoring the window contamination of the outlet window; and
- a dividing mirror arranged in the optical path between the inlet opening and the outlet opening for decoupling a part beam from the detection light as test light such that the test light is deflected to the test light receiver at least at a point in time.

12. A combination in accordance with claim 11, wherein the optical sensor has a transmission unit for the transmission of detection light into a detection region; a receiver for receiving light reflected or remitted from the detection or for receiving light transmitted through the detection region; and an evaluation unit for evaluating the received light.

* * * * *